(12) United States Patent
Freed et al.

(10) Patent No.: US 10,081,791 B2
(45) Date of Patent: Sep. 25, 2018

(54) MODELING CONNECTIONS BETWEEN DOPAMINERGIC NEURONS AND THE CEREBRAL CORTEX

(71) Applicants: William J. Freed, Bowie, MD (US); Chun-Ting Lee, Miami, FL (US)

(72) Inventors: William J. Freed, Bowie, MD (US); Chun-Ting Lee, Miami, FL (US)

( * ) Notice: Subject to any disclaimer, the term of this patent is extended or adjusted under 35 U.S.C. 154(b) by 113 days.

(21) Appl. No.: 15/148,527

(22) Filed: May 6, 2016

(65) Prior Publication Data
US 2016/0326490 A1    Nov. 10, 2016

Related U.S. Application Data

(60) Provisional application No. 62/158,302, filed on May 7, 2015.

(51) Int. Cl.
*C12N 5/0793* (2010.01)
*C12N 5/0797* (2010.01)

(52) U.S. Cl.
CPC ...... *C12N 5/0619* (2013.01); *C12N 2501/115* (2013.01); *C12N 2501/119* (2013.01); *C12N 2501/13* (2013.01); *C12N 2501/41* (2013.01); *C12N 2501/727* (2013.01); *C12N 2502/088* (2013.01); *C12N 2506/02* (2013.01); *C12N 2506/03* (2013.01); *C12N 2506/08* (2013.01)

(58) Field of Classification Search
CPC .............. C12N 5/0619; C12N 2506/02; C12N 2506/03; C12N 2506/08; C12N 2501/727; C12N 2501/115; C12N 2501/41; C12N 2501/119; C12N 2502/088; C12N 2501/13
See application file for complete search history.

(56) References Cited

U.S. PATENT DOCUMENTS

2015/0010514 A1    1/2015    Studer et al.

FOREIGN PATENT DOCUMENTS

| WO | WO 2011/130675 | 10/2011 |
|----|----------------|---------|
| WO | WO 2011/156331 | 12/2011 |

OTHER PUBLICATIONS

Bogdanowicz et al., "Multifunction Co-culture Model for Evaluating Cell-Cell Interactions," *Methods Mol. Biol.*, vol. 1202, pp. 29-36, 2014 (Author Manuscript, 10 pages).
Chen et al., "A Device for Separated and Reversible Co-Culture of Cardiomyocytes," *Biotechnol. Prog.*, vol. 26, No. 4, pp. 1164-1171, 2010 (Author Manuscript, 14 pages).
Ibidi, "Handling of Culture-Inserts," Handling of Culture Inserts, retrieved from http://ibidi.com/applications/woundhealingandmigration/handlingofcultureinserts/ on Mar. 18, 2016 (2 pages).
Kadoshima, et al., "Self-organization of axial polarity, inside-out layer pattern, and species-specific progenitor dynamics in human ES cell-derived neocortex," *PNAS*, vol. 110, No. 50, pp. 20284-20289, 2013.
Kindberg et al., "An in vitro model of human neocortical development using pluripotent stem cells: cocaine-induced cytoarchitectural alterations," *Disease Models & Mechanisms*, vol. 7, pp. 1397-1405, 2014.
Lancaster et al., "Cerebral organoids model human brain development and microcephaly," *Nature*, vol. 501, No. 7467, pp. 373-379, 2013 (Author Manuscript, 21 pages).
Lee et al., "A new technique for modeling neuronal connectivity using human pluripotent stem cells," *Restorative Neurology and Neuroscience*, vol. 33, pp. 347-356, 2015.
Zhang et al., "Differentiation of Neural Precursors and Dopaminergic Neurons from Human Embryonic Stem Cells," *Methods Mol. Biol.*, vol. 584, pp. 355-366, 2010 (Author Manuscript, 9 pages).

*Primary Examiner* — Taeyoon Kim
(74) *Attorney, Agent, or Firm* — Klarquist Sparkman, LLP (57) ABSTRACT

Disclosed are methods that include separately differentiating stem cells to form cortical neural progenitor cells and differentiating stem cells to form dopaminergic neural progenitor cells. The cortical progenitor cells are transferred to a first compartment of a culture dish and the dopaminergic progenitor cells are transferred to a second compartment of the culture dish, separated by a removable barrier. The cortical progenitor cells and dopaminergic progenitor cells are cultured in medium that promotes differentiation of cortical neurons and dopaminergic neurons, respectively. The barrier is then removed, creating a single chamber containing the cortical progenitor cells and the dopaminergic progenitor cells, separated by a gap. The cortical progenitor cells and the dopaminergic progenitor cells are then cultured in a single medium, which promotes further differentiation of the neurons and also supports formation of connections (such as synapses or synapse-like structures) between at least some of the cortical neurons and dopaminergic neurons.

20 Claims, 6 Drawing Sheets

MODELING CONNECTIONS BETWEEN DOPAMINERGIC NEURONS AND THE CEREBRAL CORTEX

CROSS REFERENCE TO RELATED APPLICATION

This claims the benefit of U.S. Provisional Application No. 62/158,302, filed May 7, 2015, which is incorporated herein by reference in its entirety.

ACKNOWLEDGMENT OF GOVERNMENT SUPPORT

This invention was made with governmental support through the National Institutes of Health. The government has certain rights in the invention.

FIELD

This disclosure relates to the field of methods for the in vitro production of differentiated neuronal cells from stem cells, such as the production of cortical cells and dopaminergic cells.

BACKGROUND

For the brain, as compared to most other organs, e.g., the liver, there are major limitations involved in examining a single neuronal cell type in isolation. Brain developmental and functional processes are highly dependent on interactions between different neural cell types and between different regions of the brain (for example, De Marco Garcia et al., Nature 472:351-355, 2011; Nishi, Prog. Neurobiol. 69:213-227, 2003). A great deal of attention has, for example, been focused on differentiation of human mesencephalic dopaminergic (mDA) neurons from human pluripotent stem cells (hPSCs) (Kriks et al., Nature 480:547-551, 2011; Perrier et al., Proc. Natl. Acad. Sci. USA 101:12543-12548, 2004; Vazin et al., PLoS One 4:e6606, 2009; Yan et al., Stem Cells 23:781-790, 2005; Zeng et al., Stem Cells 22:925-940, 2004) because of their potential for use in transplantation therapy for Parkinson's disease. The development and formation of mDA neurons does not, however, occur in isolation, and dopaminergic (DA) systems and their target structures are highly interdependent (Halliday et al., Brain Res. Mol. Brain Res. 85:171-178, 2000; Hemmendinger et al., Proc. Natl. Acad. Sci. USA 2:1264-1268, 1981; Hoffman et al., Brain Res. 274:275-281, 1983; Parish et al., J. Neurosci. 21:5147-5157, 2001; Prasad and Pasterkamp, Adv. Exp. Med. Biol. 651: 91-100, 2009; Shalaby et al., Brain Res. 307:347-350 1984).

Dopaminergic neurons play an important role in substance abuse (Volkow et al., Mol. Psychiatry 9:557-569, 2004; Wise, Biol. Psychiatry 73:819-826, 2013), motivational processes in general (Wise, Nat. Rev. Neurosci. 5:483-493, 2004), and in the pharmacotherapy of schizophrenia (Knable and Weinberger, J. Psychopharmacol. 11:123-131, 1997; Weinberger and Lipska, Schizophren. Res. 16:87-100, 1995). Both schizophrenia and substance abuse are believed to involve interactions between mDA neurons and target cells in the forebrain (Knable and Weinberger, J. Psychopharmacol. 11:123-131, 1997; Koob and Volkow, Neuropsychopharmacol. 35:217-238, 2010; Weinberger and Lipska, Schizophren. Res. 16:87-100, 1995). Therefore, the possibilities for employing either mDA neurons or neocortical neurons derived from hPSCs in isolation to elucidate substance abuse or schizophrenia are very limited.

SUMMARY

The possibilities for using individual isolated types of neurons to study complex neuronal systems, in which neurons interact with cells of various types, are limited. The availability of an hPSC-based model that would allow for the examination of mDA-cortical interactions would substantially enhance such studies. Disclosed herein is a system which allows multiple brain structures or neuronal subtypes to be produced (for example, differentiated) from a single population of hPSCs, and subsequently allowed to interact. This system is applied to the mDA projection to the neocortex, but also has the potential to be adapted for use with any two structures that can be differentiated from hPSCs.

Although there are methods available for separately culturing different types of neurons or other cells, and subsequently allowing them to interact, none are suitable for the purposes disclosed herein. The methods described herein allow two different types of neurons to be differentiated from pluripotent stem cells in the same vessel, but in separate chambers containing different media formulations and growth factors. In this system, the cells remain close enough that neuronal connections can subsequently form between the two cell types. Alternative ideas, such as the use of hydrogel or silicone barriers, or cloning rings to create a separation, are either too wide to allow for connections to subsequently develop, or too impermanent to allow cells to be differentiated over a period of several weeks during manipulations such as repeated changes in medium and addition of growth factors. Also, when neurons are differentiated in vitro they lack the developing support and scaffolding which is present in vivo, and thus may not extend axons over distances comparable to those seen during maturation of the intact brain. Thus a large gap, (e.g., >3 millimeters) between the two cell types as in currently available systems presents a substantial obstacle to the formation of connecting neurites. In addition, if two types of neurons are differentiated in two separate vessels, the process of removing the cells from a substrate and transferring them to a another vessel to allow them to interact disturbs their developing axons and dendrites, damaging the cells and interfering with their ability to adequately mature and form connections. Thus, for the purpose of studying interconnections between human neurons differentiated from human pluripotent stem cells no other known method is applicable.

The methods disclosed herein include separately differentiating stem cells to form cortical progenitor cells (such as dorsal forebrain cortical progenitor cells) and differentiating stem cells to form dopaminergic progenitor cells (such as mesencephalic dopaminergic progenitor cells). The cortical progenitor cells are then transferred to a first compartment of a culture dish and the dopaminergic progenitor cells are then transferred to a second compartment of the same culture dish, where the first compartment and the second compartment are separated by a removable barrier.

The cortical progenitor cells and dopaminergic progenitor cells separated by a barrier and are cultured in medium that promotes differentiation of cortical neurons (such as medium containing fibroblast growth factor (FGF) 18 (FGF18), neurotrophin 3 (NT3), brain derived neurotrophic factor (BDNF), and a ROCK inhibitor (such as Y-27632)) and medium that promotes differentiation of dopaminergic neurons (such as medium containing FGF8, sonic hedgehog (SHH), BDNF, and glial cell derived neurotrophic factor (GDNF)), respectively. After a period of time (such as about 5-10 days), the barrier is removed, creating a single chamber containing the cortical progenitor cells and the dopaminergic progenitor cells, separated by a gap. The cortical progenitor cells and the dopaminergic progenitor cells are then cultured in a single medium, which promotes further differentiation of the progenitor cells to cortical neurons or dopaminergic neurons and also supports formation of connections (such as synapses or synapse-like structures) between at least some of the cortical neurons and dopaminergic neurons. This final differentiation medium is constituted to facilitate both dopaminergic and cortical neuron development. In some examples, the differentiation medium contains BDNF.

The foregoing and other features of the disclosure will become more apparent from the following detailed description, which proceeds with reference to the accompanying figures.

BRIEF DESCRIPTION OF THE DRAWINGS

FIGS. 1A-1D are a series of schematics illustrating exemplary differentiation and connection protocols. FIG. 1A shows a protocol for induction of the mesencephalic dopaminergic component. The upper line indicates days of differentiation, beginning with day 0, which is the final day at which hPSCs were maintained in undifferentiated growth conditions. Abbreviations (defined in the boxed insert) below the upper line indicate differentiation stages. The lower line indicates the trophic factors which were added at each stage. FIG. 1B shows a protocol for induction of neocortical differentiation. Abbreviations below the upper line indicate differentiation stages and the trophic factors added are indicated below the lower line. FIG. 1C and 1D illustrate stages of the neuronal subtype interconnection model; numbers in italics below FIG. 1C correspond to the stages illustrated in FIG. 1D. 1: Progenitors are differentiated in separate plates. 2: Progenitors are seeded into separate compartments of ibidi dishes. In this embodiment, DFCP cells are seeded outside the removable portion (also referred to as the outer chamber) and mDP cells are seeded inside the removable portion (also referred to as the inner chamber). 3: Infection by AAV-eGFP; or other manipulations of each separate cell type can optionally be performed while the cell types remain in separate compartments, treated with different combinations of trophic factors. 4: The barrier between cell types is removed. 5: Neuronal differentiation is allowed to continue for 3 weeks, with both cell types exposed to the same media containing BDNF.

FIGS. 2A-2C is a series of digital images showing dopaminergic cell differentiation.

FIGS. 3A-3E is a series of digital images showing neocortical cell differentiation. FIG. 3A is a set of images showing characterization of neocortical neuroepithelial rosettes derived from hPSCs on day 16 of differentiation. Nestin$^+$ rosettes contain cells expressing the anterior telencephalic transcription factors OTX2 (left frame), BF1 (middle frame), and PAX6 (right frame). In contrast, the ventral telencephalic marker NKK2.1 (right frame) was not expressed. Nuclei are stained with DAPI. Scale bar=50 µm.

FIGS. 4A-4E are a series of panels showing development of projections between neocortical and DA neurons.

DETAILED DESCRIPTION

Disclosed herein is a method of arranging differentiation, plating, and trophic factor conditions which allow mDA and neocortical neurons to be differentiated from hPSCs and form connections in vitro. Although it has previously been possible for hPSCs to be induced to differentiate into multiple types of neurons, it has not been possible to produce two different kinds of neurons in the same culture vessel, because within one culture vessel different trophic factors cannot be separately applied to each neuronal progenitor population. If neuronal progenitors of different types are terminally differentiated in separate vessels, the differentiated neurons are not amenable to removal and transfer from one vessel to a separate location to allow the neurons to interact. There are various types of culture vessels which allow trophic factors to be applied to different sub-groups of cells, such as chamber slides, or "sticky" inserts, but these methods are not useful in the present situation for various reasons, such as a wide gap between the cell populations or the complications involved in transferring an entire chamber slide to a larger vessel. If, however, the two separate cells types are differentiated using a system with a removable barrier (such as the ibidi dish, as described herein), the interaction problem can be solved by removal of the cell barrier at an appropriate stage.

The model produced by the methods disclosed herein can be used to study disorders including drug abuse, schizophrenia, Parkinson's disease, and possibly eating disorders, attention deficit-hyperactivity disorder, Tourette's syndrome, and Lesch-Nyhan syndrome, which may involve dopaminergic systems (Iversen et al., *Dopamine Handbook*, Oxford University Press, 2009) with advantages as compared to the use of mDA neurons in isolation. For example, hPSC-derived mDA neurons have been used as a model of MPP+ toxicity and GDNF protection (Zeng et al., *Neuropsychopharmacol.* 31:2708-2715, 2006), but MPP+ toxicity is known to involve the fine terminal arborization of mDA terminals in the striatum, which occurs only in the presence of appropriate synaptic targets of mDA neurons as well (Feuerstetin et al., *Br. J. Pharmacol.* 95:449-458, 1988), and thus such studies might be enhanced using the model described herein. Co-cultures of mDA neurons and striatal neurons for use in studies of MPP+ toxicity can be created from rodent fetal material (Koutsilieri et al., *J. Neural Transm. Gen. Sect.* 94:189-197, 1993), but the system described herein allows for similar studies using human material. The disclosed methods, therefore, have the potential to expand the potential of hPSC-derived neurons to allow for studies of human neural systems and interconnections that have previously not been possible to model in vitro.

Among various available types of culture vessels and materials that might be adapted for this purpose, the ibidi wound-healing dish (ibidi GmbH, Munich, Germany) is a suitable vessel. Other potentially suitable vessels include chamber slides (such as Lab-Tek® chamber slides) or chambered coverslips (such as those available from Research Products International, Corp.). If chamber slides or coverslips are used, for the final differentiation phase they may be placed into a larger dish, such as a 100 mm petri dish. These alternative methods, while functional, are less desirable, as they would require large amounts of media and growth factor.

Notwithstanding the favorable properties of the ibidi type of dish, a larger amount of surface area in the chambers could be advantageous. When mDA progenitor colonies are placed into the wells, they may not distribute uniformly, and the size of the chambers of ibidi dishes is too small to allow for consistent sampling. Since the mDA progenitors used in this study do not form projections well if entirely dissociated, it is difficult to smoothly distribute cells within the small area available using the present technique. There are various other geometries of this kind of dish (for example, an annular arrangement) which might also be used in the disclosed methods. Additional advantageous geometries include any arrangement that provides a continuous length over which the two types of neurons are adjacent (though at least initially separated by a gap). Even with the available geometry of the ibidi dishes, the present technique allows two different types of neurons to be separately induced from hPSCs, and subsequently allowed to interact.

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Absence: A condition in which a particular compound or component is not present. However, the term "absence" does not require an absolute lack of the indicated compound. In some examples, "absence" of a compound includes a medium wherein exogenous compound (for example, one or more trophic factors) is not added, or medium that contains less than a particular amount of the compound (for example, less than about 25 pg/ml, such as less than about 15 pg/ml, less than about 10 pg/ml medium, less than about 5 pg/ml, or less than about 1 pg/ml). In another example, "absence" indicates that the compound (such as the one or more trophic factors) cannot be detected using a standard assay, such as an immunoassay (for example ELISA or bead-based assays) or mass spectrometry.

Brain-derived neurotrophic factor (BDNF): A protein that is a member of the nerve growth factor family. It is induced by cortical neurons and is involved in survival of striatal neurons in the brain. Exemplary nucleic acid sequences for human BDNF can be found as GenBank Accession Nos. NM_170731, NM_001143805, NM_001143806, NM_170732, NM_001143807, NM_170733, NM_001143808, NM_001143809, NM_001143810, NM_001143811, NM_001143812, NM_001143813, NM_001709, NM_001143814, NM_170734; exemplary amino acid sequences for human BDNF can be found as GenBank Accession Nos. NP_733927, NP_001137277, NP_001137278, NP_733928, NP_001137279, NP_733929, NP_001137280, NP_001137281, NP_001137282, NP_001137283, NP_001137284, NP_001137285, NP_001700, NP_001137286, NP_733930, all of which are incorporated by reference herein as present in GenBank on Apr. 27, 2015. Additional human BDNF nucleic acid and amino acid sequences include GenBank Accession Nos. NM_001143816, NM_170735, NP_001137288, and NP_733931, incorporated herein by reference as present in GenBank on Apr. 28, 2016.

Central Nervous System (CNS): The part of the nervous system of an animal that contains a high concentration of neuronal cell bodies and synapses and is the main site of integration of nervous activity. In higher animals, the CNS generally refers to the brain and spinal cord.

Cortical neurons: A cell with one or more properties characteristic of cortical neurons, for example, neurons found in the neocortex. Markers for cortical neurons and progenitor cells include the anterior telencephalic transcription factor BF1, dorsal forebrain markers PAX6 and EMX1, apical-end markers N-cadherin, CD133, and gamma-tubulin, the marker for preplate neurons TBR1, marker of lower-layer cortical neurons CTIP2, and late cortical plate neuron markers CUX1 and SATPB. Cortical neurons that employ the neurotransmitter glutamate can be identified by using antibodies directed against glutamate, or the glutamate transporters VGLUT1 and VGLUT2, while cortical neurons that employ the neurotransmitter GABA can be identified by antibodies directed against GABA, MASH1, or the GABA transporter VGAT.

Culturing or Cell Culture: Growth or maintenance of a population of cells in a defined set of conditions (such as culture medium, extracellular matrix, temperature, and/or time of culture) in vitro. In some examples, a cell culture includes a substantially pure culture (for example, isolated embryonic stem cells or isolated induced pluripotent stem cells). In additional examples a cell culture includes a mixed culture, such as co-culture of two or more types of cells (for example a culture of embryonic stem cells with a feeder layer). In further examples, a cell culture includes cells grown in contact with an extracellular matrix (such as an extracellular matrix including poly-L-ornithine and/or laminin) or cells grown in suspension culture.

Differentiation: The process whereby relatively unspecialized cells (e.g., embryonic cells and/or stem cells) acquire specialized structural and/or functional features characteristic of mature cells. Similarly, "differentiate" refers to this process. Typically, during differentiation, cellular structure alters and tissue-specific proteins and properties appear. The term "differentiated neuronal cell" refers to cells expressing a nucleic acid or protein characteristic of the specific neuronal cell type, exhibiting synaptic vesicle release, or having an electrophysiological characteristic of a neuronal cells (e.g., sustained bursts of action potentials). A differentiated neuronal cell can be a dopaminergic cell (such as a neuron with properties characteristic of dopaminergic neurons) or a cortical cell (such as a neuron with properties characteristic of cortical neurons).

Differentiation medium: A synthetic set of culture conditions with the nutrients necessary to support the growth or survival of cells, and which allows the differentiation of cells, such as stem cells.

Dopaminergic Neurons: A cell with one or more properties characteristic of dopaminergic neurons, including cells that produce the neurotransmitter dopamine. Typically, dopaminergic neurons are highly concentrated in the substantia nigra of the midbrain. Dopamine, along with epinephrine, norepinephrine, and serotonin, belongs to a chemical family referred to "monoamines." Within the family of monoamines, epinephrine, norepinephrine, and dopamine are derived from the amino acid tyrosine and form a subfamily called the catecholamines. Frequently, tyrosine hydroxylase (TH), the rate-limiting enzyme for the biosynthesis of dopamine, is used as a marker to identify dopaminergic neurons. Other markers for dopaminergic neurons include aromatic-L-amino acid decarboxylase (AADC), dopamine transporter (DAT), midbrain-specific markers LMX-1B, engrailed-1, Pitx3, Nurr-1, FOXA2, GIRK2, and MSX1.

Embryoid bodies (EB): Stem cell aggregates generated when stem cells (for example, embryonic stem cells) are plated on a non-adhesive surface that prevents attachment and differentiation of the stem cells. Generally, embryoid bodies include an inner core of undifferentiated stem cells surrounded by primitive endoderm.

Embryonic Stem Cells (ES cells or ESC): Pluripotent cells isolated from the inner cell mass of the developing blastocyst, or the progeny of these cells. ES cells can be derived from mammals, including mice, rats, rabbits, guinea pigs, goats, pigs, cows, non-human primates, and humans. In specific, non-limiting examples, the cells are human, non-human primate, or murine. Without being bound by theory, ES cells can generate a variety of the cells present in the body (bone, muscle, brain cells, etc.) provided they are exposed to conditions conducive to developing these cell types. Methods for producing murine ES cells can be found in U.S. Pat. No. 5,670,372, which is herein incorporated by reference. Methods for producing human ES cells can be found in U.S. Pat. No. 6,090,622, WO 00/70021 and WO 00/27995, which are herein incorporated by reference.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion" or "expanded." Typically, during an expansion phase, the cells do not differentiate to form mature cells.

Extracellular matrix: A substrate suitable for cell growth and/or attachment for in vitro cell culture, such as a tissue culture vessel (for example, a dish, plate, or multi-well plate). In some examples, the substrate includes a three-dimensional scaffold or matrix that supports the cells. In some examples, the substrate includes molecules that promote cell attachment, growth, differentiation, or other desirable cell properties. In particular examples, the molecules are embedded in or are present on the surface of the tissue culture vessel. In one example, the extracellular matrix includes poly-L-ornithine and/or laminin.

Feeder layer: Non-proliferating cells (e.g., irradiated cells) that can be used to support proliferation of cells, including cells obtained from diverse sources including normal as well as neoplastic tissues from humans and laboratory animals. Protocols for the production of feeder layers are known in the art, and are available on the internet, such as at the National Stem Cell Resource website, which is maintained by the American Type Culture Collection (ATCC, Manassas, Va.).

Fibroblast growth factor or FGF: Any suitable fibroblast growth factor, derived from any animal, and functional fragments thereof. A variety of FGFs are known and include, but are not limited to, FGF1 (acidic fibroblast growth factor), FGF2 (basic fibroblast growth factor, bFGF), FGF3 (int-2), FGF4 (hst/K-FGF), FGF5, FGF6, FGF7, FGF8, FGF9, FGF18, and FGF98. "FGF" refers to a fibroblast growth factor protein such as FGF1, FGF2, FGF3, FGF4, FGF5, FGF6, FGF7, FGF8, FGF9, FGF18, FGF98, or a biologically active fragment or mutant thereof. The FGF can be from any animal species. In one embodiment, the FGF is mammalian FGF, including but not limited to, rodent, avian, canine, bovine, porcine, equine, or human. The amino acid sequences and method for making many of the FGFs are well known in the art.

FGF2 (also known as bFGF or bFGF2), and other FGFs, can be made as described in U.S. Pat. No. 5,155,214. Recombinant bFGF2, and other FGFs, can be purified to pharmaceutical quality (98% or greater purity) using the techniques described in detail in U.S. Pat. No. 4,956,455. It should be noted that human and murine bFGF, FGF8, FGF18, and a variety of other FGFs, are commercially available.

An exemplary nucleic acid sequence for human bFGF can be found as GenBank Accession No. NM_002006 and an exemplary amino acid sequence can be found as GenBank Accession No. NP_001997, both incorporated by reference herein as present in GenBank on Apr. 20, 2015. Exemplary nucleic acid sequences for human FGF8 can be found as GenBank Accession Nos. NM_001206389, NM_033165, NM_006119, NM_033164, and NM_033163; exemplary amino acid sequences for human FGF8 can be found as GenBank Accession Nos. NP_001193318, NP_149355, NP_006110, NP_149354, and NP_149353, all of which are incorporated by reference herein as present in GenBank on Apr. 20, 2015. An exemplary nucleic acid sequence for human FGF18 can be found as GenBank Accession No. NM_003862 and an exemplary amino acid sequence can be found as GenBank Accession No. NP_003853, both incorporated by reference herein as present in GenBank on Apr. 20, 2015.

Glial cell derived neurotrophic factor (GDNF): A protein that promotes survival and differentiation of dopaminergic neurons in culture. GDNF is a ligand for rearranged during transfection (RET). Exemplary nucleic acid sequences for human GDNF can be found as GenBank Accession Nos. NM_000514, XM_011514029, NM_001190469, NM_001190468, NM_199231, XM_011514028, NM_001278098, XM_011514030; exemplary amino acid sequences for human GDNF can be found as GenBank Accession Nos. NP_000505, XP_011512331, NP_001177398, NP_001177397, NP_954701, XP_011512330, NP_001265027, XP_011512332, all of which are incorporated by reference herein as present in GenBank on Apr. 27, 2015.

Growth medium or expansion medium: A synthetic set of culture conditions with the nutrients necessary to support the growth (cell division/expansion) of a specific population of cells. In one embodiment, the cells are stem cells (for example, ES cells or EC cells). In this embodiment, the growth medium is a stem cell growth medium that allows stem cells to proliferate. In another embodiment, the cells are neuronal precursor cells. In this embodiment, the expansion medium is a neuronal precursor cell expansion medium that allows neuronal precursors to proliferate.

Growth media generally include a carbon source, a nitrogen source and a buffer to maintain pH. In one embodiment, stem cell growth medium contains a minimal essential media, such as DMEM, supplemented with various nutrients to enhance stem cell growth. Additionally, the minimal essential media may be supplemented with additives such as horse, calf or fetal bovine serum.

Isolated: An "isolated" biological component (such as a nucleic acid, peptide or protein) has been substantially separated, produced apart from, or purified away from other biological components in the cell of the organism in which the component naturally occurs, for example, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. In some examples, an isolated cell includes a cell that has been substantially purified from other cell types.

Neurotrophin 3 (NT3): Also known as NTF3. A protein that plays a role in survival and differentiation of neurons. Exemplary nucleic acid sequences for human NT3 can be found as GenBank Accession Nos. NM_001102654 and XM_011520963; exemplary amino acid sequences for human NT3 can be found as GenBank Accession Nos. NP_001096124 and XP_011519265, all of which are incorporated by reference herein as present in GenBank on Apr. 27, 2015. Additional human NT3 nucleic acid and amino acid sequences include GenBank Accession Nos. NM_002527 and NP_002518, respectively, both of which are incorporated herein by reference as present in GenBank on Apr. 28, 2016.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Rho-associated coiled-coil forming kinase (ROCK) inhibitor: A molecule that inhibits activity of one or more ROCKs (such as ROCK-I and/or ROCK-II). In some examples, a ROCK inhibitor is a molecule that inhibits (for example decreases) serine-threonine kinase activity of at least one member of the ROCK family of kinases. In some examples, ROCK inhibitors include Y-27632 ([(+)-(R)-trans-4-(1-aminoethyl)-N-(4-pyridyl)cyclohexanecarboxamide dihydrochloride]), fasudil, ripasudil, and Y-30141 ([(+)-(R)-trans-4-(1-aminoethyl)-N-(1H-pyrrolo[2,3-b]pyridin-4-yl)cyclohexanecarboxamide dihydrochloride]).

Rosette: A structure with a rosette-like shape, with cells in a flower petal-like arrangement, for example, expressing markers of neuroepithelial cells, including Nestin.

Sonic hedgehog (SHH): A protein involved in early embryo patterning, particularly patterning of the ventral neural tube, the anterior-posterior limb axis, and the ventral somites. Exemplary nucleic acid sequences for human SHH can be found as GenBank Accession Nos. NM_000193, XM_011516482, XM_011516479, XM_011516480, XM_011516481; exemplary amino acid sequences for human SHH can be found as GenBank Accession Nos. NP_000184, XP_011514784, XP_011514781, XP_011514782, XP_011514783, all of which are incorporated by reference herein as present in GenBank on Apr. 27, 2015.

Stem cell: A cell that can generate a fully differentiated functional cell of more than one given cell type. Generally, stem cells, such as pluripotent stem cells (for example, embryonic stem cells) can divide without limit and are capable of generating essentially all of the cell types present in a fully-developed organism. After division, the stem cell may remain as a stem cell, become a precursor cell, or proceed to terminal differentiation. A pluripotent stem cell (PSC) is a stem cell that can generate a fully differentiated cell of more than one given cell type, but is not totipotent.

A precursor cell is a cell that can generate a fully differentiated functional cell of at least one given cell type. Generally, precursor cells can divide. After division, a precursor cell can remain a precursor cell, or may proceed to terminal differentiation. A "neuronal stem cell" is a stem cell that can be differentiated into neurons. In one embodiment, a neuronal stem cell gives rise to all of the types of neuronal cells (e.g. dopaminergic, adrenergic, and serotonergic neurons) but does not give rise to other cells such as glial cells. A "neuronal precursor cell" is a precursor cell of the nervous system.

Synapse: Highly specialized intercellular junctions between neurons and between neurons and effector cells across which a nerve impulse is conducted (synaptically active). Generally, the nerve impulse is conducted by the release from one neuron (presynaptic neuron) of a chemical transmitter (such as dopamine or serotonin) which diffuses across the narrow intercellular space to the other neuron or effector cell (post-synaptic neuron). Generally neurotransmitters mediate their effects by interacting with specific receptors incorporated in the post-synaptic cell. "Synaptically active" refers to cells (e.g., differentiated neurons) which receive and/or transmit action potentials characteristic of mature neurons.

Trophic factor: A substance that promotes cell growth and/or, survival. Trophic factors include molecules that function as growth stimulators (mitogens), molecules that function as growth inhibitors (e.g., negative growth factors), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of trophic factors include FGFs, NT3, BDNF, and GDNF.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, GenBank Accession numbers, and other references mentioned herein are incorporated by reference in their entirety for all purposes. In case of conflict, the present specification, including explanations of terms, will control. In addition, the materials, methods, and examples are illustrative only and not intended to be limiting.

II. Overview of Several Embodiments

Disclosed herein are methods for culturing two different types of neuronal cells in vitro (such as cortical neuronal cells and dopaminergic neuronal cells) in order to produce connections between the two types of neuronal cells. In some examples, the connections between the cells may be synapses or are synapse-like, while in other examples, the connections may be contact between cells.

In some embodiments, the methods include separately differentiating stem cells to form cortical progenitor cells (such as dorsal forebrain cortical progenitor cells) and differentiating stem cells to form dopaminergic progenitor cells (such as mesencephalic dopaminergic progenitor cells). The cortical progenitor cells are then transferred to a first compartment of a culture dish having at least two compartments or chambers (such as a wound healing dish) and the dopaminergic progenitor cells are then transferred to a second compartment of the culture dish, where the first compartment and the second compartment are separated by a removable barrier. The cortical progenitor cells and dopaminergic progenitor cells are cultured in medium that promotes differentiation of cortical neurons and medium that promotes differentiation of dopaminergic neurons, respectively. After a period of time (such as about 5-10 days), the barrier is removed, creating a single chamber containing the cortical progenitor cells and the dopaminergic progenitor cells, separated by a gap. In some examples, the gap created by removing the barriers is less than 3 mm wide (for example, less than 2.5 mm, less than 2 mm, less than 1.5 mm, less than 1 mm, or less than 0.5 mm wide). In other examples, the gap is about 0.2-3 mm wide (such as about 0.3-2 mm, 0.5-1.5 mm, 0.5-1 mm, 1-1.5 mm, 1-3 mm, or 1-2 mm wide).

The cortical progenitor cells and the dopaminergic progenitor cells are then cultured in the same medium, which promotes further differentiation of the progenitor cells to cortical neurons or dopaminergic neurons and also supports formation of connections (such as synapses or synapse-like structures) between at least some of the cortical neurons and dopaminergic neurons (such as culture in medium containing BDNF). A specific example of the disclosed methods is shown schematically in FIGS. 1A-1D. Specific (non-limiting) exemplary methods are also described in Example 1.

A. Production of Cortical Neuron Progenitor Cells

In some embodiments of the methods disclosed herein, cortical progenitor cells are produced in a separate vessel and then transferred to a first compartment of the culture dish having at least two compartments separated by a removable barrier. Cortical progenitor cells can be produced from stem cells (such as embryonic stem cells or induced pluripotent stem cells) by any suitable method. In a particular embodiment, cortical progenitor cells are produced by culturing human pluripotent stem cells (such as ES04 or CT2 cells) under non-adherent conditions in the absence of added bFGF for a period of time to allow formation of embryoid bodies (such as about 1-6 days, about 3-5 days, or about 4 days). The embryoid bodes are then cultured in the presence of bFGF (such as about 5-50 ng/ml bFGF, for example about 10-40 ng/ml, or about 20 ng/ml) for about 1-3 days and then grown in adherent culture (for example on laminin-coated plates) in the same medium for about 5-15 days (such as about 8-12 days or about 10 days), resulting in formation of neural rosettes. Rosettes are isolated, dissociated to colonies of about 25-150 µm (such as about 50-100 µm) and cultured in suspension culture in the same medium for about 2-4 days (such as about 3 days).

B. Production of Dopaminergic Neuron Progenitor Cells

In some embodiments of the methods disclosed herein, dopaminergic neuron progenitor cells are produced in a separate vessel and then transferred to a second compartment of the culture dish having at least two compartments separated by a removable barrier.

Dopaminergic progenitor cells can be produced from stem cells (such as embryonic stem cells or induced pluripotent stem cells) by any suitable method. In a particular embodiment, dopaminergic progenitor cells are produced by culturing human pluripotent stem cells (such as ES04 or CT2 cells) are grown under non-adherent conditions in the absence of added bFGF for a period of time to allow formation of embryoid bodies (such as about 1-6 days, about 3-5 days, or about 4 days). The embryoid bodes are then cultured in the presence of bFGF (such as about 5-50 ng/ml bFGF, for example about 10-40 ng/ml, or about 20 ng/ml) for about 1-3 days and then grown in adherent culture (for example on laminin-coated plates) in the same medium for about 3-10 days (such as about 4-8 days, 3-7 days, or about 5 days). The cells are then cultured in medium containing FGF8 (such as about 10-100 ng/ml FGF8, for example, about 20-80 ng/ml, about 30-60 ng/ml, or about 50 ng/ml) for about 5-10 days (such as about 4-8 days, or about 7 days), resulting in formation of neural rosettes. Rosettes are isolated and grown in the same medium for about 1-4 days (such as 2-3 days) as floating aggregates, followed by addition of SHH to the medium (for example, about 100-500 ng/ml SHH, about 200-400 ng/ml, about 100-300 ng/ml, or about 200 ng/ml) for about 5-10 days (such as about 6-8 days, or about 7 days).

C. Culture of Cortical and Dopaminergic Progenitor Cells in Separate Chambers

Cortical neuron progenitor cells and dopaminergic neuron progenitor cells are seeded in first and second compartments, respectively, of a culture dish with a removable barrier between the compartments (such as an ibidi dish). In particular embodiments disclosed herein, the cortical progenitor cells are seeded in an outer chamber and the dopaminergic progenitor cells are seeded in an inner chamber of a culture dish with a removable barrier between the inner and outer chambers. In other examples, the dopaminergic progenitor cells are seeded in an outer chamber and the cortical progenitor cells are seeded in an inner chamber of a culture dish with a removable barrier between the inner and outer chambers. If an ibidi dish is utilized (for example as described in Example 1), the dopaminergic progenitor cells can be seeded in one inner chamber of the culture dish and the cortical progenitor cells can be seeded in the other inner chamber of the culture dish, which has a removable barrier between the two inner chambers (see FIG. 1D).

The progenitor cells are then cultured under conditions that promote further differentiation of the progenitor cells to cortical neurons or dopaminergic neurons, as discussed below. The presence of the removable barrier between the compartments permits culture of the cortical progenitor cells and dopaminergic progenitor cells in different media that includes trophic factors and/or other factors appropriate to the differentiation of the individual types of progenitor cells.

Colonies produced from the rosettes of cortical progenitor cells (for example, produced as described in Section A, above) are seeded on adherent plates (such as poly-ornithine/laminin coated plates) in a first compartment of the culture dish and are cultured with medium containing FGF18, NT3, BDNF, and a ROCK inhibitor for about 3-10 days (for example, about 4-8 days, about 3-6 days, about 5-7 days, or about 7 days. In some examples, the medium includes about 5-50 ng/ml FGF18 (for example about 10-40 ng/ml, or about 20 ng/ml), about 5-50 ng/ml NT3 (for example about 10-40 ng/ml, or about 20 ng/ml), about 5-50 ng/ml BDNF (for example about 10-40 ng/ml, or about 20 ng/ml), and about 1-100 µM of a ROCK inhibitor (for example, about 1-50 µM, about 5-25 µM, about 1-10 µM, or about 10 µM). In one example, the ROCK inhibitor is Y-27632. Other exemplary ROCK inhibitors include fasudil, ripasudil, and Y-30141.

Aggregates of dopaminergic progenitor cells (for example, produced as described in Section B, above) are seeded in a second compartment of the culture dish and are cultured with medium containing FGF8, SHH, BDNF, and GDNF for about 3-10 days (for example, about 4-8 days, about 3-6 days, about 5-7 days, or about 7 days. In some examples, the medium includes about 5-50 ng/ml FGF8 (for example about 10-40 ng/ml, or about 20 ng/ml), about 100-500 ng/ml SHH (for example about 200-400 ng/ml, about 100-300 ng/ml, or about 200 ng/ml), about 1-25 ng/ml BDNF (for example about 5-20 ng/ml, or about 10 ng/ml), and about 1-25 ng/ml GDNF (for example about 5-20 ng/ml, or about 10 ng/ml).

If the period of differentiation of the dopaminergic progenitor cells is short enough to allow the cells to be removed and transferred to a separate vessel, later stages of differentiation could be carried out in the two-compartment chamber without further disturbing or detaching the cells. Thus, in some examples, the dopaminergic progenitor cells can be at least partially differentiated prior to their transfer to a compartment of the culture dish having at least two compartments separated by a removable barrier. For example, the dopaminergic progenitor cells may be cultured in medium containing FGF8, SHH, BDNF, and GDNF for several days (for example about 1-4 days) prior to transfer. In general, if this protocol is utilized, it is desirable to transfer the partially differentiated dopaminergic progenitor cells before they start to extend axons and/or dendrites, as these are likely to be damaged during transfer.

D. Formation of Connections between Cortical and Dopaminergic Neurons

Following culture of the progenitor cells in the first and second compartments of the culture dish, the removable barrier between the compartments is removed. Removal of the barrier creates a single compartment including populations of each type of cells, which are separated by a gap that does not include any cells. The cortical and dopaminergic cells are then cultured in a single medium, which in some examples, includes about 5-50 ng/ml BDNF (for example about 10-40 ng/ml, about 15-30 ng/ml, or about 20 ng/ml BDNF). The cells are cultured in the medium containing BDNF for a period of time sufficient for formation of connections between at least one cortical neuron and at least one dopaminergic neuron. In some examples, the cells are cultured in the medium containing BDNF for at least one week (for example, about 1-12 weeks, about 1-10 weeks, about 2-8 weeks, or about 3-6 weeks).

In some embodiments, projections extend from one type of neuron (such as a dopaminergic neuron) to the other type of neuron (such as a cortical neuron), for example across the gap between the populations of cells. In one example, the projections include elaborated processes with the appearance of terminal arborization. In other examples, the projections make functional contacts between the neurons, which can be determined using electrophysiology techniques (for example, by stimulating one set of the cells and recording from the other set of cells).

III. Stem Cells

A stem cell is a cell that can generate a partially or fully differentiated functional cell of more than one given cell type. Stem cells include embryonic stem (ES) cells (for example, primate ES cells, such as human ES cells), embryonal carcinoma (EC) cells (for example, human EC cells), neuronal stem cells, or neuronal stem cells.

Embryonic stem cells can proliferate indefinitely in an undifferentiated state. Furthermore, ES cells are pluripotent cells, meaning that they can generate all of the cells present in the body (bone, muscle, brain cells, etc.). ES cells have been isolated from the inner cell mass (ICM) of the developing murine blastocyst (Evans et al., *Nature* 292:154-156, 1981; Martin et al., *Proc. Natl. Acad. Sci.* 78:7634-7636, 1981; Robertson et al., *Nature* 323:445-448, 1986). Additionally, human cells with ES properties have been isolated from the inner blastocyst cell mass (Thomson et al., *Science* 282:1145-1147, 1998) and developing germ cells (Shamblott et al., *Proc. Natl. Acad. Sci. USA* 95:13726-13731, 1998), and human and non-human primate embryonic stem cells have been produced (see U.S. Pat. No. 6,200,806, which is incorporated by reference herein).

Human ES cell lines exist and can be used in the methods disclosed herein. Any human or non-human primate ES cell or pluripotent stem cell can be utilized with the methods disclosed herein (see U.S. Pat. No. 6,200,806, which is incorporated by reference in its entirety). In some examples, the methods described herein utilize previously derived hES cell lines. One cell line suitable for differentiation to dopaminergic and/or cortical neurons by the disclosed methods is the BG01 cell line and derivatives of the BG01 cell line, such as BG01V, BG01V2, BG02, and BG03 cell lines (BresaGen; Athens, Ga.). In some examples, hES cell lines include ES04, CT2, H1, H7, H9, hES1, SNUhES1, SNUhES3, SNUhES16, SA002, HE3, HSF6, EB5, CCE, and derivatives of these cell lines. One of skill in the art can select additional hES cell lines that can be used with the methods described herein to produce dopaminergic neuronal cells and/or cortical neuronal cells. In particular examples, ES04 and/or CT2 cells lines are used in the methods disclosed herein.

In other examples, mouse ES cells may also be utilized with the methods described herein. Mouse embryonic stem cells (mESCs) are pluripotent cells derived from the inner cell mass of day 3.5 blastocysts. They can be maintained in vitro for extended periods without loss of their capacity to contribute to all cell lineages when reimplanted back into a blastocyst. mESCs can also be differentiated into various cell types, including dopaminergic neuronal cells, in vitro. Methods of producing mESCs are well known to one of skill in the art (see, e.g., *Manipulating the Mouse Embryo A Laboratory Manual*, Second Edition, Cold Spring Harbor Laboratory Press (1994)). Mouse ES cell lines are well known to one of skill in the art. Exemplary mESCs include, but are not limited to, R1, E14.1, and B5 cell lines. One of skill in the art can select additional mES cell lines that can be used with the methods described herein to produce dopaminergic neuronal cells and/or cortical neuronal cells.

In additional examples, the methods described herein may be utilized with induced pluripotent stem (iPS) cells. These cells are pluripotent cells that have been reprogrammed to an embryonic-like state; iPS cells have been generated from mouse embryonic and adult fibroblasts; human fetal, newborn, and adult fibroblasts; and primate (rhesus macaque) adult fibroblasts. See e.g., Takahashi and Yamanaka, *Cell* 126:663-676, 2006; Okita et al., *Nature* 448:313-317, 2007; Wernig et al., *Nature* 448:318-324, 2007; Yu et al., *Science* 318:1917-1920, 2007; Takahashi et al., *Cell* 131:861-872, 2007; Liu et al., *Cell Stem Cell* 3:587-590, 2008. iPS cells are similar to ESCs in that they are capable of differentiation into multiple tissue types (including neurons and cardiomyocytes), formation of teratomas and embryoid bodies, and germline competency. Methods for producing iPS cells (for example, mouse or human iPS cells) are known in the art. See, e.g., Takahashi and Yamanaka, *Cell* 126:663-676, 2006; Yu et al., *Science* 318:1917-1920, 2007; Takahashi et al., *Cell* 131:861-872, 2007; Liu et al., *Cell Stem Cell* 3:587-590, 2008. Exemplary iPS cell lines include iPS (IMR90), iPS(Foreskin), iPS-DF19-9, iPS-DF4-3, and iPS-DF6-9 cell lines. iPS cell lines are available, for example, from the WiCell International Stem Cell Bank (Madison, Wis.).

IV. Characterization of Differentiated Cells

The neuronal cells and structures (e.g., neuronal connections) resulting from the methods described herein can be characterized by methods known in the art, including assessing cell morphology, gene expression, cytoarchitecture, and/or cellular activity. In some examples, cells produced by differentiation of stem cells using the methods described herein are neuronal cells, such as cortical neuronal cells and/or dopaminergic neuronal cells.

Neuronal cells can be identified by expression of neuronal markers, including, but not limited to microtubule-associated protein-2 (MAP-2), Noggin, nestin, β-III tubulin, neurofilament proteins (for example, neurofilament light, medium, or heavy proteins), synapsin, synaptophysin, and growth-associated protein 43. Other suitable neuronal markers can be selected by one of skill in the art.

In some examples, the methods disclosed herein produced cortical neuronal cells. Cortical neuronal cells can be identified by expression of cortical neuron markers, including, but not limited to the anterior telencephalic transcription factor BF1, dorsal forebrain markers PAX6 and EMX1, apical-end markers N-cadherin, CD133, and gamma- tubulin, the marker for preplate neurons TBR1, marker of lower-layer cortical neurons CTIP2, and late cortical plate neuron markers CUX1 and SATPB. Cortical neurons which employ the neurotransmitter glutamate can be identified by using antibodies directed against glutamate, or the glutamate transporters VGLUT1 and VGLUT2, while cortical neurons which employ the neurotransmitter GABA can be identified by antibodies directed against GABA, MASH1, or the GABA transporter VGAT. Other suitable markers can be selected by one of skill in the art.

In additional examples, the methods disclosed herein produce dopaminergic (DA) neuronal cells. In some examples, DA neuronal cells can be identified by their morphology, such as fusiform or multipolar cells (see e.g., Berger et al, *Neuroscience* 7:193-205, 1982; Grace and Onn *J. Neurosci.* 9:3463-3481, 1989). DA neuronal cell morphology can be identified by one of skill in the art. DA neuronal cells are also identified by expression of DA neuron markers, including, but not limited to the enzymes of the dopamine synthetic pathway (e.g., TH and AADC (also known as DOPA decarboxylase)) and the dopamine transporter (DAT). DA neuronal cells also express midbrain neuronal markers, such as Lmx 1b, Pitx3, En1 and receptors such as GFR1, c-RET, TrkB, and Smo. Additional markers for DA neuronal cells can include forkhead box A1 (FOXA1), forkhead box A2 (FOXA2), IGF2, MSX1, NK2 homeobox 2 (NKX2-2), NK6 homeobox 1 (NKX6-1), orthodenticle homeobox 2 (OTX2), SRY (sex determining region Y)-box 1, SRY (sex determining region Y)-box 2 wingless-type, MMTV integration site family member 1 (Wnt1), and aldehyde dehydrogenase 1 family, member A1 (ALDH 1A1). Other suitable DA neuronal markers can be selected by one of skill in the art. Thus, in some examples, the dopaminergic cells express TH and/or other DA neuronal cell markers.

Methods of detecting expression of particular markers in a cell or cell population are well known in the art. In some examples, gene expression is assessed by measuring the amount of a nucleic acid (such as mRNA or cDNA) present in a sample, such as a differentiated stem cell. Methods of detecting a target nucleic acid molecule (such as RNA or DNA, for example mRNA or cDNA) in a sample are well known in the art. For example, nucleic acid amplification methods (with the appropriate probes and primers), as well as nucleic acid arrays (containing the appropriate probes), can be used. For example, the level of gene expression can be determined or even quantified utilizing methods well known in the art, such as Northern blots, RNase protection assays, nucleic acid arrays, reverse transcription-PCR, quantitative PCR (such as quantitative real-time PCR or Taq-Man® assays), dot blot assays, in situ hybridization, or combinations thereof. Gene expression can also be assessed by determining the amount of a protein present in a sample, such as a differentiated stem cell. Methods of detecting a protein in a sample are well known in the art. For example, immunoassays (for example, Western blotting or ELISA) and immunocytology (for example, immunohistochemistry or flow cytometry) methods can be used.

In additional examples, cells produced by the methods described herein are identified by assessing cellular activity, for example by electrophysiology. Electrophysiological methods are well known in the art and include voltage clamp recording and patch clamp recording. In some examples, the cells exhibit action potentials under current clamp conditions. In other examples, the cells exhibit large voltage-gated sodium currents and/or delayed rectifier potassium currents. In particular examples DA neuronal cells exhibit voltage-gated currents (such as sodium and/or potassium currents) and currents in response to neurotransmitters (such as GABA and/or glutamate). In additional examples, DA neuronal cells may exhibit a hyperpolarization-activated inward current (h-current or $I_f$; see, e.g., Silva et al., *J. Neuro-*

*physiol.* 64:262-272, 1990; Mercuri et al., *Euro. J. Neurosci.* 7:462-469, 1995; Lin and Lipski, *J. Neurophysiol.* 85:1336-1339, 2001).

The disclosure is illustrated by the following non-limiting examples:

EXAMPLE 1

Methods hPSC culture: hESC lines ES04 (P65-69; ES Cell International, Singapore) and CT2 (P88-90; University of Connecticut Stem Cell Core) were propagated in feeder-dependent culture, using irradiated mouse embryonic fibroblasts (MEF, Global Stem). hESCs were cultured in hESC medium, containing DMEM/F12 with 20% Knockout Serum Replacement (KSR), 2 mM L-Glutamine, Pen/Strep (50 U/ml and 50 µg/ml, respectively), 2 mM nonessential amino acids, 0.1 mM β-mercaptoethanol, and 4 ng/ml bFGF (all from Invitrogen). Colonies were passaged using 1 mg/ml Collagenase Type IV (Invitrogen) every 5 days (1:3 split ratio). Cell karyotype analyses were routinely performed on twenty G-banded metaphase cells.

Dopaminergic neuron differentiation: hPSCs were differentiated to mDA neurons (FIG. 1A) using an adaptation of the method described by Yan et al. (*Stem Cells* 23:781-790, 2005). Briefly, undifferentiated hPSC colonies (day 0) were grown as floating EBs in hESC medium without bFGF for four days. On day 4 the floating EBs were transferred to neural media containing DMEM/F-12 (2:1) with N2 supplement, 0.1 mM non-essential amino acids, 2 µg/ml heparin, supplemented with 20 ng/ml bFGF (Invitrogen) from days 4-6, and were then grown in adherent culture in same media from days 6-10. On day 10, bFGF was replaced with 50 ng/ml FGF8 (R&D), and the cells were maintained in this medium until day 16. On day 16, neural rosettes were isolated by manual dissection and grown as floating NE aggregates in neural medium supplemented with 50 ng/ml FGF8 for 2 days, followed by addition of 50 ng/ml FGF8 and 200 ng/ml SHH (R&D) from days 18-24. On day 24, NE aggregates were seeded on poly-ornithine/laminin-coated inner compartments of ibidi chambers (ibidi GmbH, Munich, Germany) and maintained in neurobasal medium containing N2 supplement, 0.1 mM non-essential amino acids, 0.5 mM L-Glutamine, 2 µg/ml heparin, 1 µM cAMP, 1 µg/ml laminin, and 200 µM ascorbic acid and supplemented with FGF8 (50 ng/ml), SHH (200 ng/ml, R&D), BDNF (10 ng/ml, R&D), and GDNF (10 ng/ml, R&D) until removal of the barrier on day 31 of differentiation.

Neocortical neuron differentiation: Neocortical differentiation was performed according to the protocol illustrated in FIG. 1B, essentially as described by Kindberg et al. (*Dis. Model Mech.* 7:1397-1405, 2014) except that cells were dissociated on day 19, and at that time the Rock inhibitor Y-27632 was added to the cultures. In brief, hPSC colonies were grown in non-adherent conditions in hESC medium without bFGF for four days, allowing EB formation. The EBs were then transferred to neural media containing DMEM/F-12 (2:1) with N2 supplement, 0.1 mM non-essential amino acids, and 2 µg/ml heparin, supplemented with 20 ng/ml bFGF for two additional days (day 6). Colonies were then grown in adherent culture, on laminin-coated plates, in the same media with 20 ng/ml bFGF from days 6 to 16. On day 16 dorsal cortical rosettes were isolated by manual dissection, dissociated into 50-100 µm diameter colonies, and maintained in suspended culture in the same medium with 20 ng/ml bFGF before being seeded on poly-ornithine/laminin coated dishes at day 19. On day 19, colonies were dissociated using Accutase® cell detachment solution for 20 minutes at 37° C., washed using neural media, and placed into the outer compartment of the ibidi chambers in neurobasal medium containing B27 supplement, 0.1 mM non-essential amino acids, 0.5 mM L-Glutamine, and 2 µg/ml heparin but with the addition of FGF18 (20 ng/mL, Biosource), NT3 (20 ng/mL, R&D), BDNF (20 ng/mL, R&D) and the ROCK inhibitor Y-27632 (10 µM, Stemgent) until the barrier was removed on day 26 of differentiation.

Figure 1A:
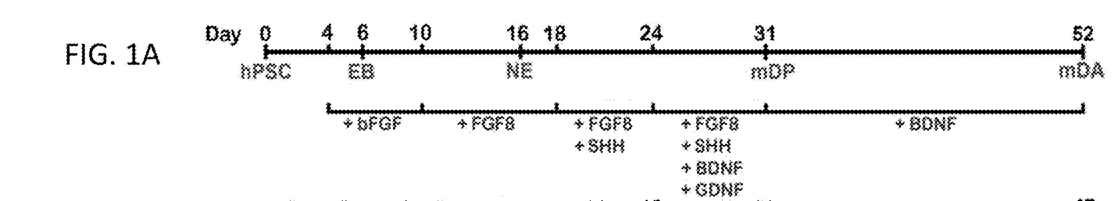
Figure 1B:
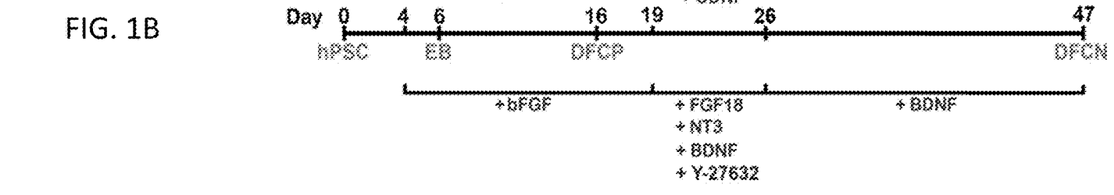
Figure 1C:
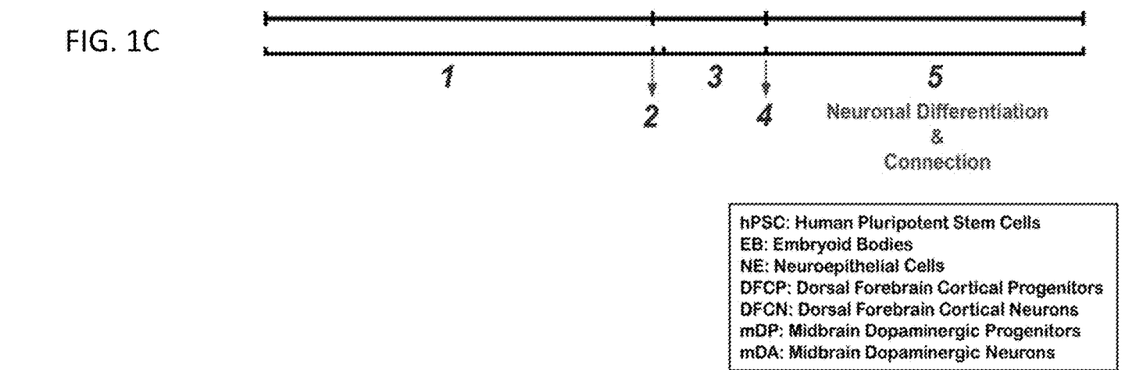

Connection formation: Connections between the mDA and neocortically-differentiated components was accomplished using the ibidi wound healing dish (ibidi GmbH, Munich, Germany). These dishes are optimized for studies of wound healing, using dissociated keratinocytes or fibroblasts. The day at which the barrier between the inner and outer chambers was removed was day 31 for mDA differentiation, and day 26 for neocortical differentiation, as indicated in FIGS. 1A-1C. On the day of barrier removal, the medium was changed and replaced with neurobasal medium containing B27 supplement, 0.1 mM non-essential amino acids, 0.5 mM L-Glutamine, and 2 µg/ml heparin, containing 20 ng/ml BDNF, and no other trophic factors.

Immunocytochemistry: Cells were fixed with 4% PFA for 10 min, washed with PBS, and blocked with 0.2% Triton®-X in PBS supplemented with 5% BSA and 10% goat/donkey serum. Cells were then incubated with primary antibodies in 0.2% Triton®-X in PBS with 5% BSA and 5% goat/donkey serum: rabbit anti-LMX1A (1:2,000, Millipore), goat anti-FOXA2 (1:50; Santa Cruz), rabbit anti-TH (1:500; Pel-Freez), mouse anti-TUJ1 (1:2,000; Promega), rabbit anti-TUJ1 (1:2,000; Covance), rabbit anti-OTX2 (1:1000; Millipore), mouse anti-Nestin (1:50; R&D), rabbit anti-BF1 (1:100; Abcam), mouse anti- NKX2.1 (1:200; Chemicon), rabbit anti-PAX6 (1:300; Covance), rabbit anti-Glutamate (1:2000; Sigma), rabbit anti-VGLUT1 (1:500; Synaptic Systems), rabbit anti-VGLUT2 (1:500; Synaptic Systems), mouse anti-GABA (1:100, Sigma), and rabbit anti-VGAT (1:500; Synaptic Systems). Corresponding fluorescent-labeled secondary antibodies were used (Alexa-Fluor 488 for green, Alexa-Fluor 555 for red; R&D). Images were captured using a Carl Zeiss Axiovert 200M (Jena, Germany) microscope.

AAV viral transduction: The construction of pdsAAVGFP has been described previously (Wang et al., *Gene Ther.* 10:2105-2111, 2003). Vectors were packaged based on triple transfection method (Xiao et al., *J. Virol.* 72:2224-2232, 1998) as previously described (Howard et al., *Virology* 372:24-32, 2008). To provide the rep/cap genes for producing serotypes 2 and 6, pXX2 (Xiao et al., 1998) and pAAV2/6 (Rabinowitz et al., *J. Virol.* 76:791-801, 2002) were used respectively. Both AAV2 and AAV6 were purified by CsC1 ultracentrifugation and tittered using real-time PCR as previously described (Howard et al., 2008). A multiplicity of infection of 10,000 to 20,000 was used for transduction. The transduction efficiency was more than 80% as assessed by microscopic observation.

EXAMPLE 2

Differentiation of Dopaminergic and Neocortical Neurons

This example describes differentiation of mesencephalic dopaminergic neurons and neocortical neurons from hPSCs.

Figure 2A:
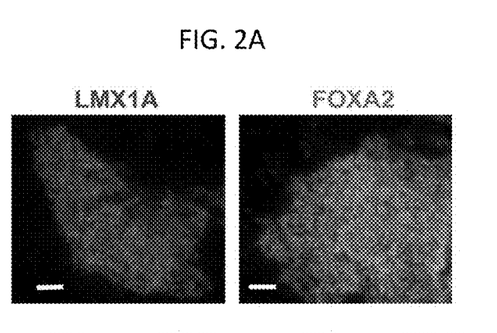
FIG. 2A is a pair of panels showing expression of LMX1A (left) and FOXA2 (right) transcription factors for mesencephalic DA progenitor cells, at day 31, prior to removal of the barrier between cell types. Scale bar=50 µm.
Figure 2B:
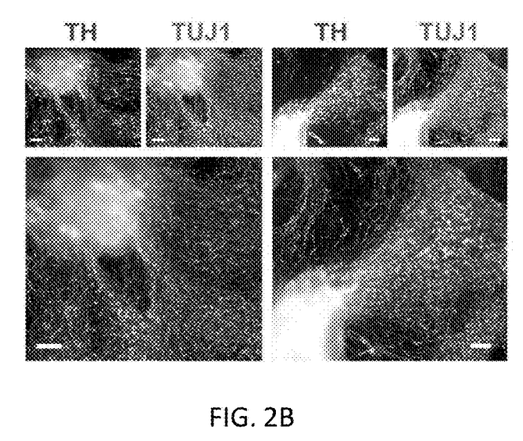
FIG. 2B is a series of panels showing expression of TH and TUJ1 by immunocytochemistry at day 52, for mDA neurons differentiated according to the protocol shown in FIG. 1A, showing projections extending from colonies positive for TH and TUJ1. Scale bar=100 µm.
Figure 2C:
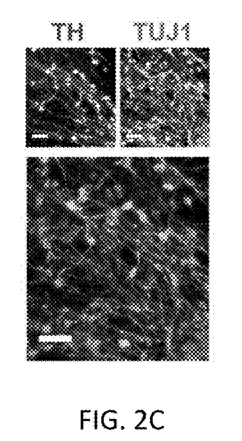
FIG. 2C is a series of panels showing higher magnification images of mDA neurons differentiated for 52 days showing individual TH-positive and TUJ1-positive neurons. Scale bar=50 µm. Cell line: ES04.

For differentiation of mDA cells from hPSCs as illustrated in FIG. 1A, colonies of mDA progenitor cells at day 31 expressed the mDA transcription factors LMX1A and FOXA2 (FIG. 2A). When allowed to differentiate for 52 days (FIG. 1A), in neurobasal medium with B27 supplement including BDNF as the only added trophic factor from days 31-52, the colonies contained numerous TH$^+$ and TUJ1$^+$ neurons (FIGS. 2B and 2C). The colonies remained largely intact, with clusters of TH$^+$ fiber projections present at day 52 (FIG. 2B). At day 52, TH$^+$ neurons comprised approximately one third of the total TUJ1+ cells (FIG. 2C).

Figure 3A:
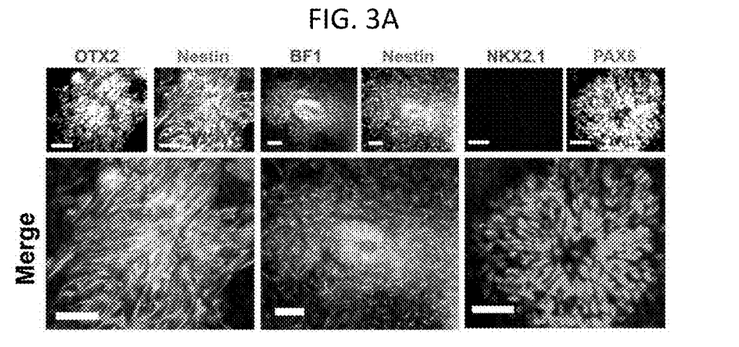
Figure 3B:
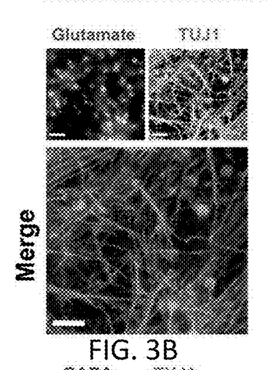
FIG. 3B is a set of images showing immunocytochemical staining for glutamate and TUJ1 on day 47 of differentiation using the current protocol, as shown in FIG. 1B. Scale bar=25 µm.
Figure 3C:
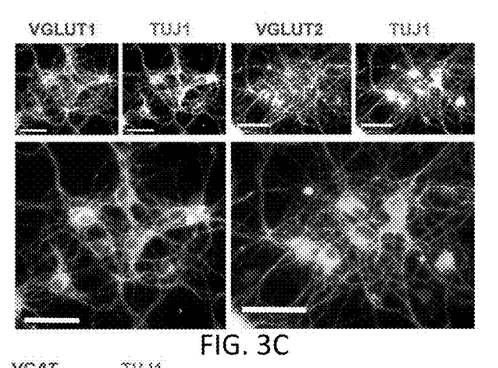
FIG. 3C is a set of images showing that TUJ1$^+$ neurons were positive for the vesicular glutamate transporters VGLUT1 (left frame) and VGLUT2 (right frame) on day 47 of differentiation. Nuclei were stained with DAPI. Scale bar=50 µm.
Figure 3D:
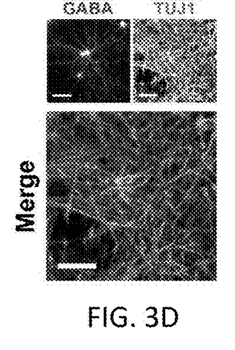
FIG. 3D is a set of images showing expression of GABA and TUJ1 by immunocytochemistry on day 47 of differentiation. Scale bar=100 µm.
Figure 3E:
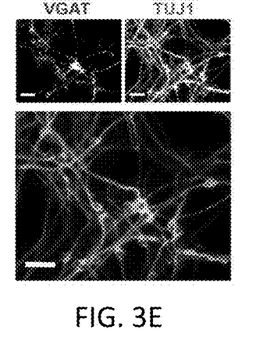
FIG. 3E is a set of images showing expression of the GABA transporter VGAT and TUJ1 by immunocytochemistry on day 47 of differentiation. Scale bar=25 µm. Cell line: ES04.

For differentiation of neocortical neurons from hPSCs, as illustrated in FIG. 1B Nestin$^+$ neuroepithelial rosettes expressed the anterior telencephalic transcription factors OTX2 and BF1, and the dorsal forebrain marker PAX6, but did not express the ventral telencephalic marker NKX2.1 (FIG. 3A). At the end of differentiation, on day 47 for neocortical differentiation, the majority of TUJ1$^+$ neurons had adopted a glutamatergic phenotype (FIG. 3B), expressing the vesicular glutamate transporters VGLUT1 and VGLUT2 (FIG. 3C). On day 47 the differentiated population also included a small population of GABA-containing neurons (FIG. 3D) expressing VGAT (FIG. 3E).

EXAMPLE 3

Formation of Connections between Dopaminergic and Neocortical Neurons

This example describes formation of connections between mDA and neocortical neurons.

Figure 1D:
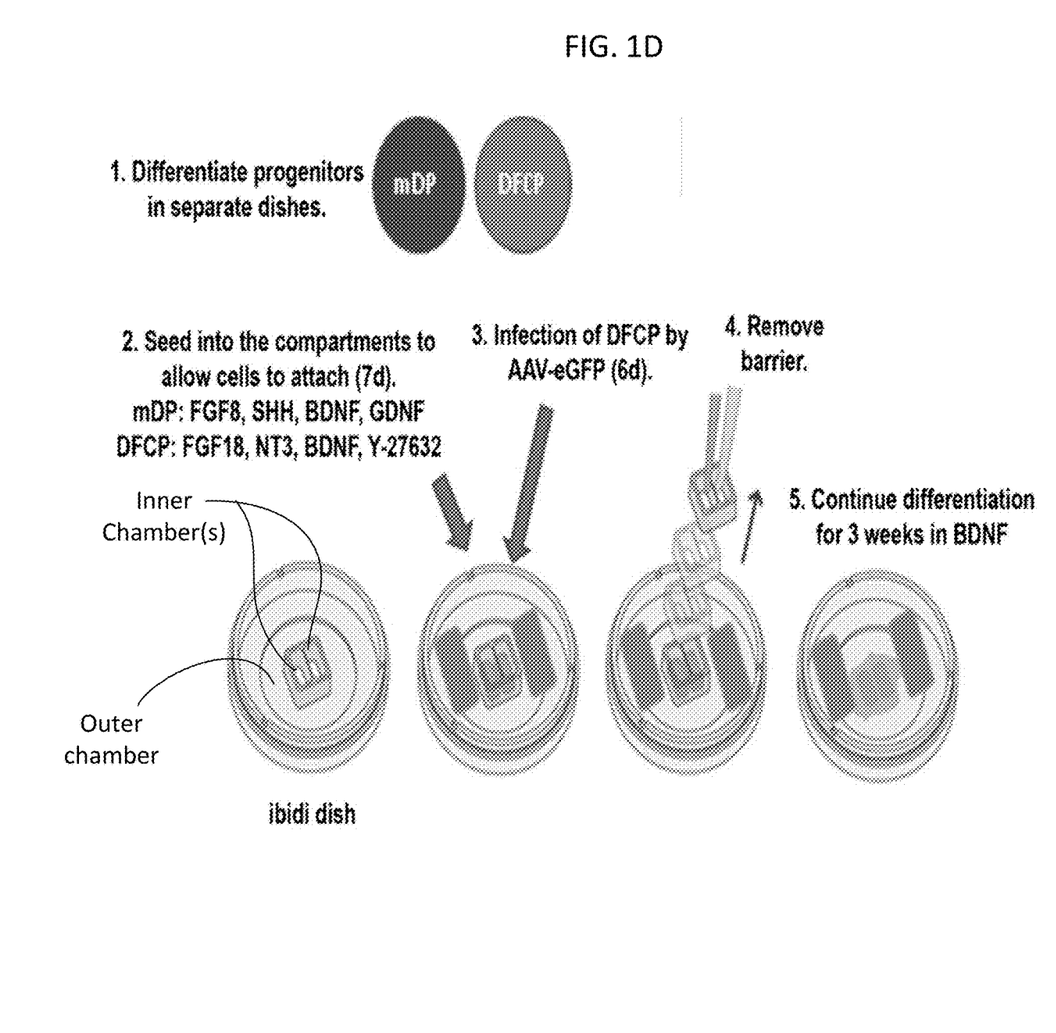
Figure 4A:
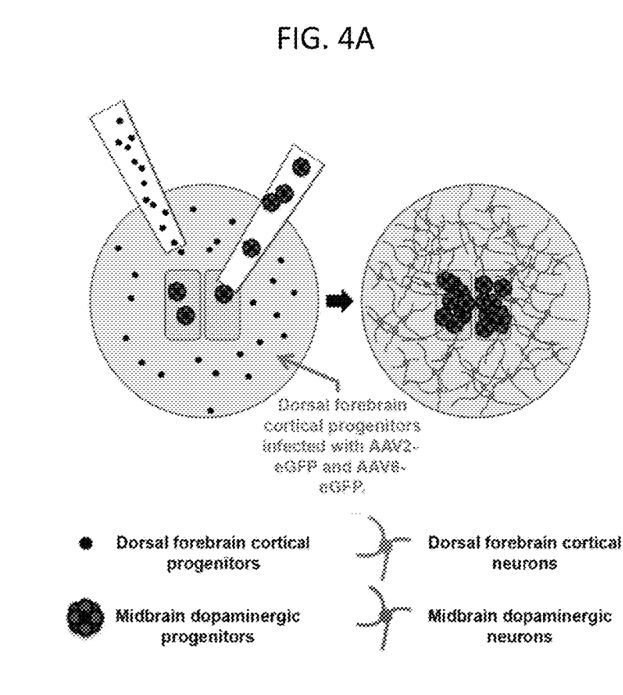
FIG. 4A is a schematic illustration of the process of progenitor seeding into separate chambers (e.g., mDP in the inner chamber(s) and mDFCP in the outer chamber), and development of connections after removal of the barrier between chambers.
Figure 4B:
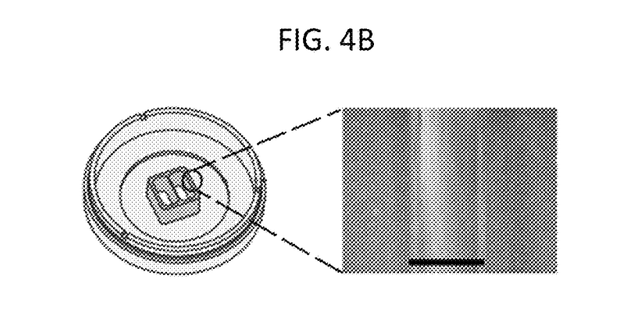
FIG. 4B is a schematic illustration of the gap between the inner and outer chambers after removal of the barrier (courtesy of ibidi GmbH, Planegg, Germany). Phase contrast image, scale bar=500 µm.
Figure 4C:
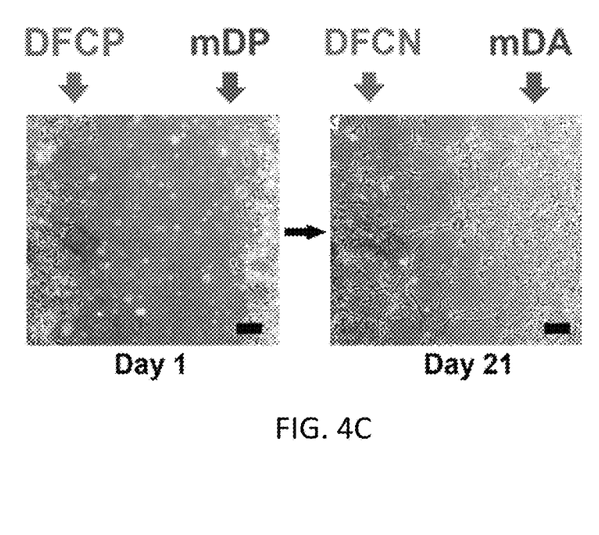
FIG. 4C is a pair of phase contrast images of the gap between the inner and outer chambers on day 1 after removal of the barrier (left) and after 21 days (right). The gap between DA and neocortical neurons persists on day 21 although some cells and projections are seen between the two regions. Scale bar=100 µm.
Figure 4D:
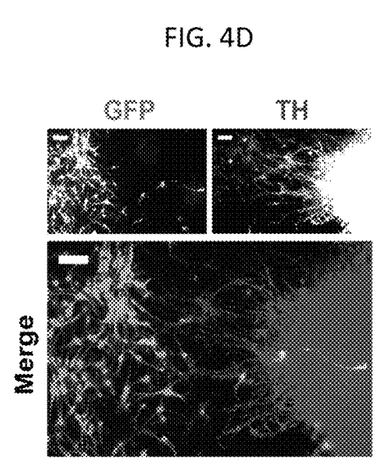
FIG. 4D is a set of images showing an example of TH-positive projections from the inner chamber to the area of the outer chamber after 21 days. Scale bar=100 µm.
Figure 4E:
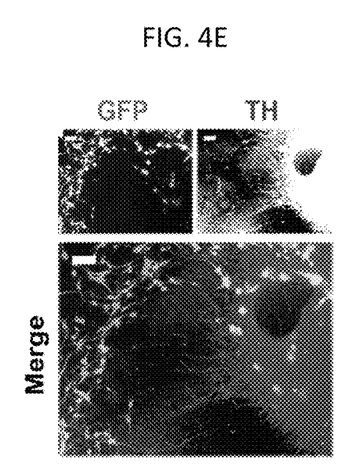
FIG. 4E is a set of images showing an example of TH-positive projection forming a fine terminal arborization among GFP$^+$ neocortical cells, seen in the lower left of the merged image. Scale bar=100 µm. Neocortical neurons were labelled with AAV-eGFP. Some eGFP-positive cells migrated across the gap, to the inner area, and were interspersed with TH-positive neurons. Cell line: CT2.

To build the connection between mDA and neocortical neurons as illustrated in FIGS. 1C and 1D, the general distribution of progenitors within the inner and outer chambers is illustrated in FIG. 4A. The appearance of the gap between the inner and outer chambers is shown in FIG. 4B. After the progenitors were seeded into ibidi chambers on day 24 of mDA differentiation and day 19 of neocortical differentiation, each type of progenitors was further differentiated using mDA-specific and neocortex-specific trophic factors for 1 week. After the barrier was removed, neuronal differentiation was continued for an additional 3 weeks using the same culture conditions for both neuronal subtypes: neurobasal medium with B27 supplement containing 20 ng/mL BDNF, but with no other trophic factors. At the end of differentiation, neurons retained their phenotypic identity and largely remained in their respective locations on each side of the barrier with few cells having migrated across the gap between the chambers, to the other side (FIGS. 4C-4E). As can be seen in FIG. 4C the gap between the two different neuronal populations narrowed over time, and some cells had moved into the area vacated by the barrier.

Neocortical progenitors were infected using both AAV2- and AAV6-eGFP for 6 days, and about 80% of neocortical neurons were positive for GFP at the end of differentiation (FIGS. 1C-1D; FIGS. 4D-4E). Immunostaining and fluorescence imaging showed that a few GFP neocortical cells had migrated into the area of mDAergic TH$^+$ neurons, while conversely a few TH$^+$ cells were seen in the area of the outer chamber, among the GFP$^+$ neocortical neurons. Nonetheless, the majority of cells remained in the areas of the inner and outer chambers respectively. In areas where groups of TH$^+$ neurons were in proximity to GFP$^+$ neocortical neurons, TH$^+$ projections were seen to have extended outward from the DA neurons, crossing the gap and extending into the area of neocortical neurons (FIG. 4D). In some cases the TH$^+$ neurons had elaborated processes which had the appearance of terminal arborization (FIG. 4E, lower left), resembling that which is seen in DA target areas of the rat brain (e.g., Matsuda et al., *J. Neurosci.* 29:444-453, 2009).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of producing an in vitro system in which there are connections between one or more cortical neurons and one or more dopaminergic neurons, comprising:
    culturing cortical neuron progenitor cells in a first compartment of a culture dish and culturing dopaminergic neuron progenitor cells in a second compartment of the culture dish, wherein the first compartment and the second compartment are separated by a removable barrier that creates a gap;
    removing the barrier; and
    culturing the cortical neuron progenitor cells and the dopaminergic neuron progenitor cells in a medium comprising 5-50 ng/ml brain-derived neurotrophic factor (BDNF) and no other added trophic factors under conditions sufficient to produce differentiation of the cortical neuron progenitor cells to cortical neurons and differentiation of the dopaminergic neuron progenitor cells to dopaminergic neurons, wherein the at least one of the cortical neurons forms a connection with at least one of the dopaminergic neurons.

2. The method of claim 1, wherein culturing the cortical neuron progenitor cells in the first compartment comprises culturing the cortical neuron progenitor cells in the presence of fibroblast growth factor 18 (FGF18), neurotrophin 3 (NT3), brain-derived neurotrophic factor (BDNF), and ROCK-inhibitor Y-27632.

3. The method of claim 2, wherein the cortical neuron progenitor cells are cultured in the presence of FGF18, NT3, BDNF, and Y-27632 for 7 days.

4. The method of claim 2, wherein the cortical neuron progenitor cells are cultured in the presence of 20 ng/ml FGF18, 20 ng/ml NT3, 20 ng/ml BDNF, and 10 μM Y-27632.

5. The method of claim 1, wherein culturing the dopaminergic neuron progenitor cells in the second compartment comprises culturing the dopaminergic neuron progenitor cells in the presence of fibroblast growth factor 8 (FGF8), sonic hedgehog (SHH), brain-derived neurotrophic factor (BDNF), and glial cell derived neurotrophic factor (GDNF).

6. The method of claim 5, wherein the dopaminergic neuron progenitor cells are cultured in the presence of FGF8, SHH, BDNF, and GDNF for 7 days.

7. The method of claim 5, wherein the dopaminergic neuron progenitor cells are cultured in the presence of 50 ng/ml FGF8, 200 ng/ml SHH, 10 ng/ml BDNF, and 10 ng/ml GDNF.

8. The method of claim 1, wherein the cortical neuron progenitor cells and the dopaminergic neuron progenitor cells are cultured with 20 ng/ml BDNF and no other added trophic factors after the barrier is removed.

9. The method of claim 1, wherein the cortical neuron progenitor cells and the dopaminergic neuron progenitor cells are cultured in the presence of BDNF and no other added trophic factors for 7-28 days after the barrier is removed.

10. The method of claim 1, wherein the connection between at least one of the cortical neurons and at least one of the dopaminergic neurons is a synapse or synapse-like structure.

11. The method of claim 1, wherein the cortical progenitor cells cultured in the first compartment are produced by:
    culturing embryonic stem cells or induced pluripotent stem cells to form embryoid bodies; and
    culturing the embryoid bodies in the presence of a fibroblast growth factor under conditions sufficient to produce cortical progenitor cells.

12. The method of claim 11, wherein the embryoid bodies are cultured in the presence of 20 ng/ml basic fibroblast growth factor (bFGF).

13. The method of claim 11, wherein culturing the embryonic stem cells or induced pluripotent stem cells to form embryoid bodies comprises culturing the stem cells in the absence of added bFGF for during formation of embryoid bodies.

14. The method of claim 1, wherein the dopaminergic progenitor cells cultured in the second compartment are produced by:
    culturing embryonic stem cells or induced pluripotent stem cells to form embryoid bodies;
    culturing the embryoid bodies in the presence of at least one fibroblast growth factor under conditions sufficient to form rosettes;
    isolating the rosettes; and
    culturing the rosettes in suspension culture in the presence of fibroblast growth factor 8 (FGF8).

15. The method of claim 14, wherein culturing the embryonic stem cells or induced pluripotent stem cells to form embryoid bodies comprises culturing the stem cells in the absence of added bFGF for during formation of embryoid bodies.

16. The method of claim 14, wherein the embryoid bodies are cultured in the presence of bFGF and/or FGF8.

17. The method of claim 16, wherein the embryoid bodies are cultured in the presence of bFGF for about 6 days and subsequently cultured in the presence of FGF8 for about 6 days.

18. The method of claim 14, wherein the rosettes are cultured in the presence of FGF8 for about 2 days and subsequently cultured in the presence of FGF8 and SHH for about 6 days.

19. A method of producing an in vitro system in which there are connections between one or more cortical neurons and one or more dopaminergic neurons, comprising:
    (a) culturing cortical neuron progenitor cells in a first compartment of a culture dish in the presence of 20 ng/ml FGF18, 20 ng/ml NT3, 20 ng/ml BDNF, and 10 µM Y-27632 for 7 days; and
    culturing dopaminergic neuron progenitor cells in a second compartment of the culture dish in the presence of 50 ng/ml FGF8, 200 ng/ml SHH, 10 ng/ml BDNF, and 10 ng/ml GDNF for 7 days,
    wherein the first compartment and the second compartment are separated by a removable barrier that creates a gap;
    (b) removing the barrier; and
    (c) culturing the cortical neuron progenitor cells and the dopaminergic neuron progenitor cells in the presence of 20 ng/ml BDNF and no other added trophic factors for 7-28 days after the barrier is removed to produce differentiation of the cortical neuron progenitor cells to cortical neurons and differentiation of the dopaminergic neuron progenitor cells to dopaminergic neurons, wherein the at least one of the cortical neurons forms a connection with at least one of the dopaminergic neurons.

20. The method of claim 1, wherein the medium containing 5-50 ng/ml BDNF and no other added trophic factors is neurobasal medium with B27 supplement.

* * * * *